United States Patent [19]
Kenten et al.

[11] Patent Number: 5,981,216
[45] Date of Patent: Nov. 9, 1999

[54] TRANSFORMED MYELOMA CELL-LINE AND A PROCESS FOR THE EXPRESSION OF A GENE CODING FOR A EUKARYOTIC POLYPEPTIDE EMPLOYING SAME

[75] Inventors: John Henry Kenten, High Wycombe; Michael Alan Boss, Ruislip, both of United Kingdom

[73] Assignee: Alusuisse Holdings A.G., Rheinfall, Switzerland

[21] Appl. No.: 08/483,813

[22] Filed: Jun. 7, 1995

Related U.S. Application Data

[62] Division of application No. 07/701,374, May 13, 1991, which is a continuation of application No. 06/939,130, filed as application No. PCT/GB86/00187, Apr. 1, 1986, abandoned.

[30] Foreign Application Priority Data

Apr. 1, 1985 [GB] United Kingdom .................. 8508442
Sep. 3, 1985 [GB] United Kingdom .................. 8521815

[51] Int. Cl.$^6$ ...................................................... C12P 21/06
[52] U.S. Cl. ........................ 435/69.1; 435/70.2; 435/352; 435/353; 435/354
[58] Field of Search ................................. 435/69.1, 69.9, 435/70.21, 91, 240.1, 320.1, 70.2, 352, 353, 354; 536/24.1; 935/32, 34, 56, 57, 60

[56] References Cited

U.S. PATENT DOCUMENTS

| | | | |
|---|---|---|---|
| 4,663,281 | 5/1987 | Gillies et al. | 435/68 |
| 4,740,461 | 4/1988 | Kaufman | 435/68 |
| 4,775,624 | 10/1988 | Bang et al. | 435/226 |

FOREIGN PATENT DOCUMENTS

| | | | |
|---|---|---|---|
| 0043718 | 1/1982 | European Pat. Off. | |
| 0255320 | 2/1988 | European Pat. Off. | C12N 15/00 |

OTHER PUBLICATIONS

Gillies et al., "A tissue–specific transcription enhancer element is located in the major intron of a rearranged immunoglobulin heavy chain enhancer", Cell, 33: 717–728, Jul. 1983.

Mulligan and Berg, "Expression of a bacterial gene in mammalian cells", Science, 209: 1422–1427, Sep. 1980.

*Catalogue of Cell Lines and Hybridomas*, 6th ed. pp. 152, 158, 178 (1988).

Gorman, C. et al., "The Rous Sarcoma Virus Long Terminal Repeat is a Strong Promoter when Introduced into a Variety of Eukaryotic Cells by DNA–Mediated Transfection", Proc. Natl. Acad. Sci. (USA), 79: 6777–6781 (1982).

Hamer et al., "Regulation In Vivo of a Cloned Mammalian Gene: Cadmium Induces the Transcription of a Mouse Metallothionein Gene in SV40 Vectors", *J. Mol. Appl. Genet.*, vol. 1, No. 4, pp. 273–288 (1982).

Kudo, A. et al., "A Cloned Human Immunoglobulin Heavy Chain Gene with a Novel Direct–Repeat Sequence in 5' Flanking Regions", *Gene*, vol. 33, No. 2, pp. 181–189, Feb. 1985.

Mulligan, R. C. et al., "Selection for Animal Cells that Express the *Escherichia coli* Gene Coding for Xanthine–Guanine Phosphoribosyltransferase", *Proc. Natl. Acad. Sci. (USA)*, vol. 78, No. 4, pp. 2072–2076, Apr. 1981.

Palmiter, R. D. et al., "Metallothionein–Human GH Fusion Genes Stimulate Growth of Mice", *Science*, vol. 222, pp. 809–814, Nov. 18, 1983.

Perkins, A. et al., "Design of a Retrovirus–Derived for Expression and Transduction of Exogenous Genes in Mammalian Cells", *Molecular and Cellular Biology*, vol. 3, No. 6, pp. 1123–1132, Jun. 1983.

Sarver N. et al., "Bovine Papilloma Virus Deoxyribonucleic Acid: A Novel Eucaryotic Cloning Vector", *Molecular and Cellular Biology*, 1: 486–496 (1981).

Serfling, E. et al., "Enhancers and Eukaryotic Gene Transcription", *Trends in Genetics*, pp. 224–230, Aug. 1985.

Shulman, M. et al., "A Better Cell Line for Making Hybridomas Secreting Specific Antibodies", *Nature*, vol. 276, pp. 269–270, Nov. 16, 1976.

*Primary Examiner*—Nancy Degen
*Assistant Examiner*—Irem Yucel
*Attorney, Agent, or Firm*—Venable; John W. Schneller; Lawrence J. Carroll

[57] ABSTRACT

A myeloma cell-line transformed with a vector including a gene coding for a eukariotic polypeptide and a non-immunolglobulin promoter such that expression occurs of the gene coding for the eukariotic polypeptide, directed by the non-immunoglobulin promoter. The promoter may be a viral promoter, such as an SV40 promoter, a Rous sarcoma virus long terminal repeat or a Moloney murine leukemia long terminal repeat, or a non-viral promoter such as the mouse metallothionein promoter. Rat and mouse host myeloma cell-lines such as the rat YB/2/3.0 Ag20 hybridoma, the mouse SP-20 Ag hybridoma and the mouse NSO hybridoma are employed. The production of tissue plasminogen activator (tPA) is exemplified.

10 Claims, 3 Drawing Sheets

FIG. 1A pSV2β globin 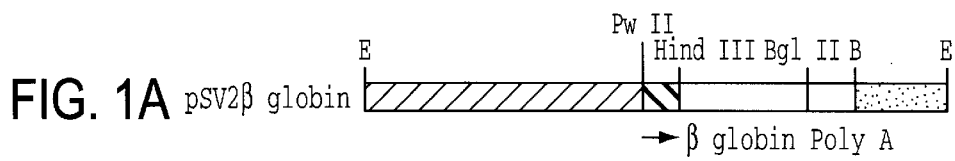
FIG. 1B pSV3B ne 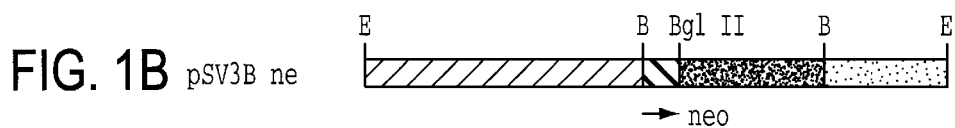
FIG. 1C pSV3 mmne 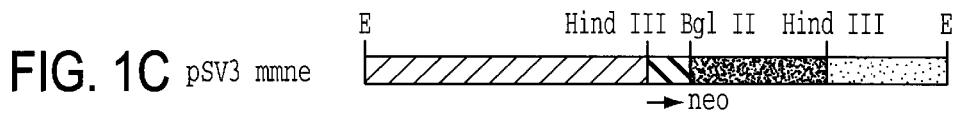
FIG. 1D p6 / pRSV3 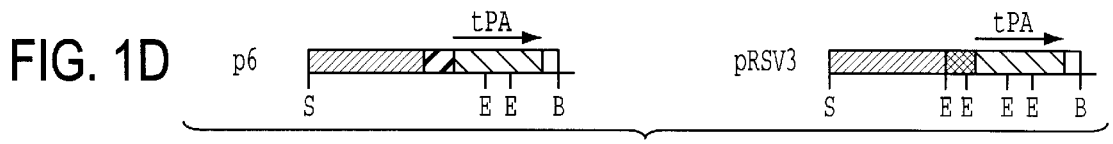
FIG. 1E p3·16 / pZAP7 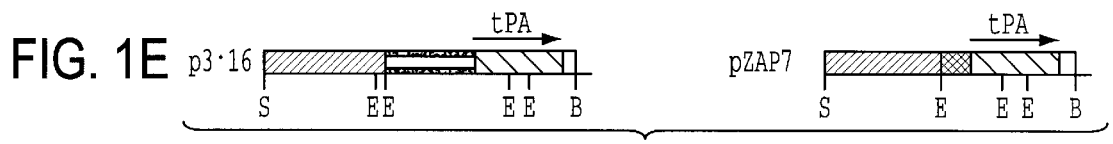
FIG. 1F pAC1 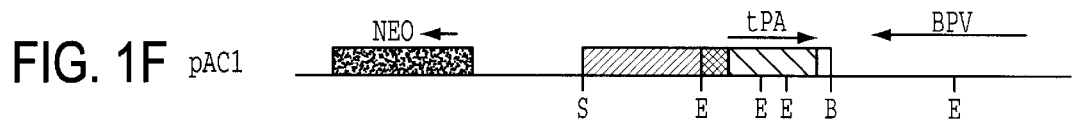
FIG. 1G pAC2 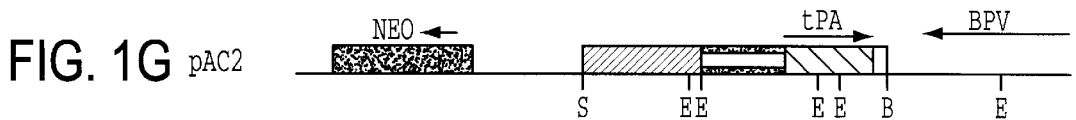
FIG. 1H pAC5 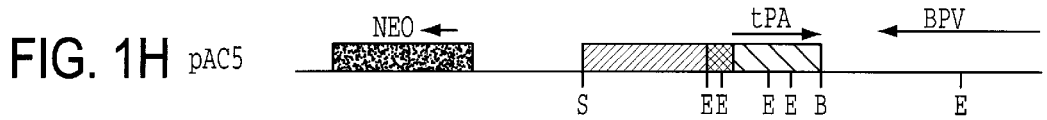
FIG. 1I pAC6 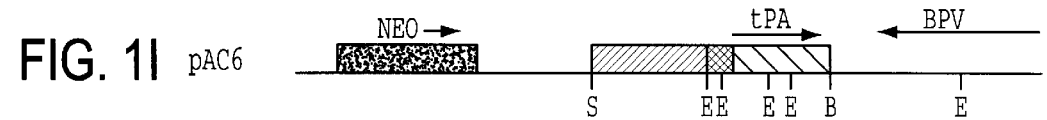
FIG. 1J pPR1 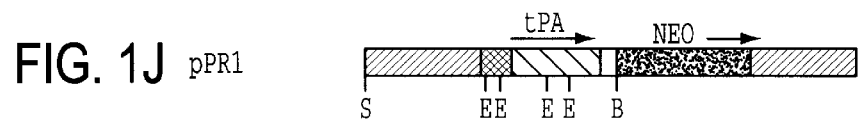

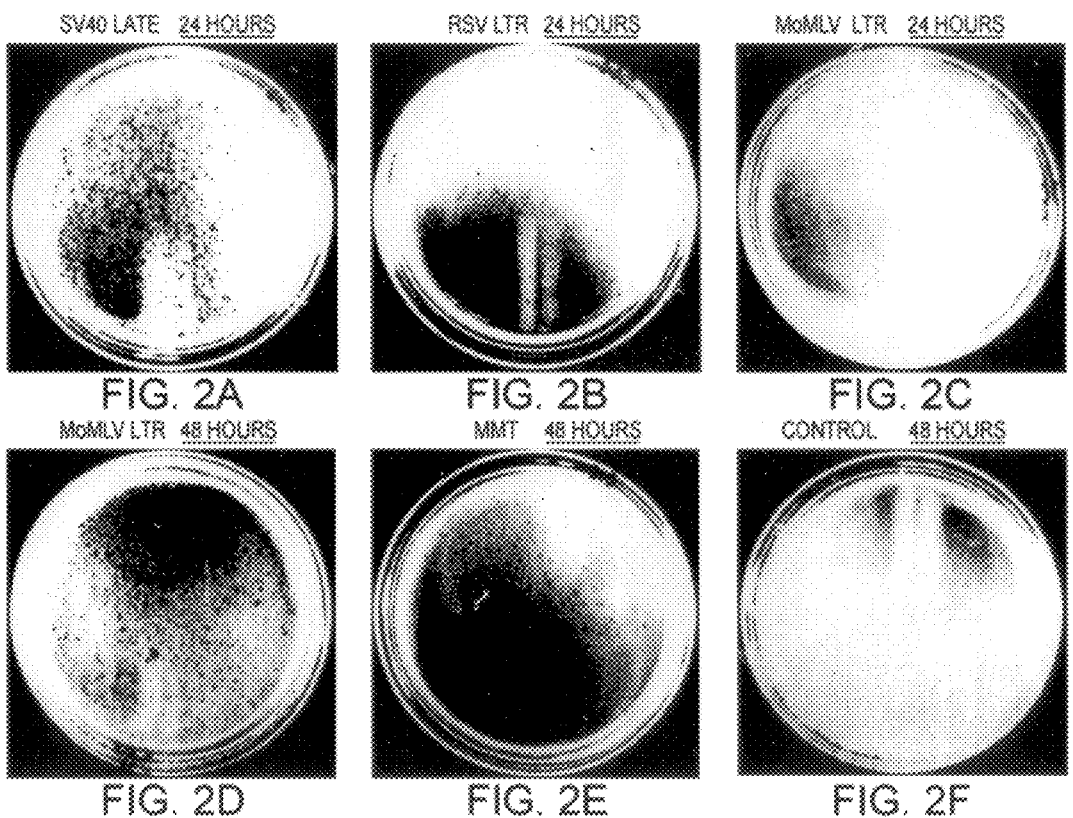

TRANSFORMED MYELOMA CELL-LINE AND A PROCESS FOR THE EXPRESSION OF A GENE CODING FOR A EUKARYOTIC POLYPEPTIDE EMPLOYING SAME

This is a Division of application Ser. No. 07/701,374 filed May 13, 1991 which is a Continuation of application Ser. No. 06/939,130 filed Nov. 24, 1986, now abandoned which is the National Stage entry of PCT/GB86/00187, filed Apr. 1, 1986.

FIELD OF THE INVENTION

This invention relates to the field of recombinant DNA biotechnology. In particular, it relates to transformed myeloma cell-line and to a process for the expression of a gene coding for a eukaryotic polypeptide in myeloma cells.

BACKGROUND TO THE INVENTION

In recent years, advances in biotechnology have led to an ability to produce eukaryotic polypeptides on an industrial scale by the expression of appropriate genes in the cells of host cell-lines. The commercial success of such processes depends upon the efficiency with which a particular gene can be expressed in the cells of a given host cell-line. There is a continued need for expression systems exhibiting high expression efficiency.

Early expression experiments were conducted using bacterial cell-lines. However, the disparity between such cellular environments and the normal environment of eukaryotic polypeptides leads to some undesirable effects and generally to a low product output. These effects have been, to some extent, ameliorated by the use of eukaryotic cell-lines, particularly mammalian cell-lines, as hosts. A variety of mammalian cell-line expression systems are known (see for example U.S. Pat. No. 4,419,446 (Howley, et al) which describes the transformation of mouse fibroblast cells with a vector including a gene coding for human insulin).

Studies relating to the expression of immunoglobulin genes have involved the use of recombinant DNA techniques to clone the relevant genes and to transform mammalian cells with the cloned genes. (Morrison, S. L. and Oi, V. T. Ann Rev. Immunol. (1984) 2 239–256). Myeloma cell-lines have been used as hosts and various vectors have been produced to transform myeloma cell-lines. These vectors in general carry an immunoglobulin promoter and gene. The vectors also include selectable markers to allow selection of host myeloma cells which have been successfully transformed. The markers comprise viral promoters driving expression of prokaryotic genes coding for non-secreted products which confer antibiotic resistance on transformed host cells. The products, which have a catalytic inactivating effect upon antibiotics, are produced at low levels.

These studies have shown that myeloma cell-lines exhibit a very specialised function in the expression of immunoglobulin genes. It has been shown that chimaeric mouse/human immunoglobulins can be produced in myeloma cells (Morrison, S. L. et al PNAS USA (1984) 81 6851–6588; Neuberger, M. S. Nature (1985) 314 268–270; Boulianne, G. L. Nature (1984) 312 643–646) and also that chimaeric immunoglobulin/enzyme and immunoglobulin/antigen polypeptides can be produced in myeloma cells. In all cases, an immunoglobulin promoter is used to direct expression of the desired product which comprises, at least in part, an immunoglobulin.

It has now been surprisingly discovered that it is possible to express eukaryotic genes at high levels in myeloma cell-lines from non-immunoglobulin promoters. This result is surprising in view of the specialised nature of myeloma cells and the known dependence upon cell type of the expression of eukaryotic genes.

SUMMARY OF THE INVENTION

According to a first aspect of the invention there is provided a myeloma cell-line transformed with a vector including a gene coding for a eukaryotic polypeptide and a non-immunoglobulin promoter, such that expression occurs of the gene coding for the eukaryotic polypeptide directed by the non-immunoglobulin promoter.

According to a second aspect of the present invention there is provided a process for preparing a eukaryotic polypeptide comprising culturing myeloma cells transformed with a vector including a gene coding for the eukaryotic polypeptide and a non-immunoglobulin promoter, such that when the vector is transformed into myeloma cells, expression occurs of the gene coding for the eukaryotic peptide, directed by the non-immunoglobulin promoter.

The vector, which may be a plasmid and which may be an episomal vector, but is preferably an integration vector, includes a selectable marker, such as a resistance marker. The resistance marker may be placed near to the site of insertion of the heterologous coding sequence and is preferably under the control of a separate promoter, for example an SV40 promoter. The resistance marker may be replaced with or supplemented with an amplifiable gene such as the gene coding for dihydrofolate reductase (dhfr).

The promoter is preferably a viral promoter, most preferably derived from a retrovirus, for example, a long terminal repeat (LTR) derived from such a retrovirus. Examples of suitable promoters are a Simian virus 140 (SV40) promoter preferably the late SV40 promoter and the Rous sarcoma virus long terminal repeat (RSV LTR). The RSV LTR is a DNA sequence which has previously been described as a strong promoter when introduced into a variety of eukaryotic cells such as fibroblast cell-lines (Gorman, et al (1982) PNAS 79 6777–6781). However, due to the specialised nature of myeloma cells, it is entirely unexpected that the RSV LTR proves effective in a myeloma cellular environment.

Alternatively the promoter may be non-viral, such as the mouse metallothionein promoter.

The term "myeloma" as used herein encompasses mammalian myeloma cells and cells derived therefrom by fusion, such as hybridoma type cell-lines.

The eukaryotic polypeptide may be a mammalian polypeptide such as an enzyme (for example, chymosin), an enzyme inhibitor, a hormone (for example, growth hormone), a lymphokine (for example, an interferon), or an immunoglobulin or a fragment thereof (for example a fab fragment).

The eukaryotic polypeptide may be a fusion polypeptide comprising at least in part a eukaryotic polypeptide. The eukaryotic polypeptide may be in a naturally occurring form or in the form of a functionally equivalent derivative. The eukaryotic polypeptide may include a signal sequence allowing export of the polypeptide from the host myeloma cell.

In the embodiment described below by way of example, the eukaryotic polypeptide is tissue plasminogen activator (tPA), an especially preferred product.

Particular expression vectors of the invention are designated p6, p3.16, pRSV3, pZAP7, pAC1, pAC2, pAC5 p6GD, p6gpt, pR5D3, pAC6 and pRI, the construction of which form available materials is described in detail below.

The myeloma cell-line may be a rat or mouse myeloma or hybridoma cell-line, such as the rat YB2/3.0 Ag20 hybridoma cell-line, the mouse NSO hybridoma cell-line or the mouse SP2-0Ag hybridoma cell-line.

We have discovered that certain combinations of myeloma cell-lines with vectors carrying specific promoters exhibit advantageous properties. Preferably when the cell-line is a rat cell-line, such as the rat YB/3.0 Ag20 hybridoma cell-line, the promoter used is the RSV LTR. Preferably where the cell-line is a mouse cell-line, such as the mouse SP2-OAg hybridoma, the mouse NSO hybridoma cell-line or an NSO-derived hybridoma cell-line, the promoter used is the SV40 late promoter.

Where the eukaryotic polypeptide includes the relevant signal sequences (at least in the initially translated product) export of the polypeptide occurs to the culture supernatant, allowing an improved process which does not require cell disruption to harvest the product.

The process for preparing a eukaryotic polypeptide may comprise isolating the polypeptide from the culture supernatant of a culture of myeloma cells transformed with a vector of the invention such that expression of the gene and secretion of the polypeptide product occurs.

Rat hybridoma cell-line YB2/3.0 Ag20 is described in British patent specification 2079313 and is on deposit at the American Type Culture Collection (as YB2/O or YB2/3HL. P2. G11. 16Ag.20) under Accession Number CRL1662 (Data of deposition earlier than Jun. 1, 1985).

Mouse hybridoma cell-line SP2-OAg14 is on deposit at the American Culture Collection under Accession Number CRL1581 (Data of deposition earlier than Jun. 1, 1985).

Mouse hybridoma cell-line P3/NS1/1 Ag4.0 (the NS1 cell-line) is on deposit at the American Culture Collection under Accession Number T1B18 (Date of deposition).

BRIEF DESCRIPTION OF DRAWINGS

The invention is now described with reference to the accompanying drawings in which:

FIGS. 1A–1J show restriction maps of plasmids pSV2 B globin, pSV3 Bne, pSV3 MMne, p6, P3.16, pRSV3, pZAP7, pAC1, pAC2, pAC5, pAC6 and pPR1 (The direction of transcription of the tPA and BPV genes is denoted by arrows. The positions of the restriction enzyme sites for EcoRI, BamHI and SalI are denoted E, B and S respectively. The origin of the various sequences are denoted:—BPV ▒pBR322 derived DNA; ☐mouse metallothionein promoter; ▓LTR promoters from either mouse Moloney leukaemia virus (pACI, pAC3) or Rous Sarcoma virus (pAC4, pAC5, pAC6 and pPR1); ▨tPA cDNA gene; ☐ SV40 polyA site; ▨SV40 late promoter; ▬ selection gene; ▨SV40 early promoter; ▨SV40 sequences).

FIGS. 2A–2F comprise photographs of fibrin agarose plates containing cells (SP2/O-Ag14) transfected with identical plasmid constructs, except for promoter fragments 5' of the tPA gene, at times 24 hours and 48 hours from the start of transfection.

DESCRIPTION OF SPECIFIC EMBODIMENTS

Figure 3:
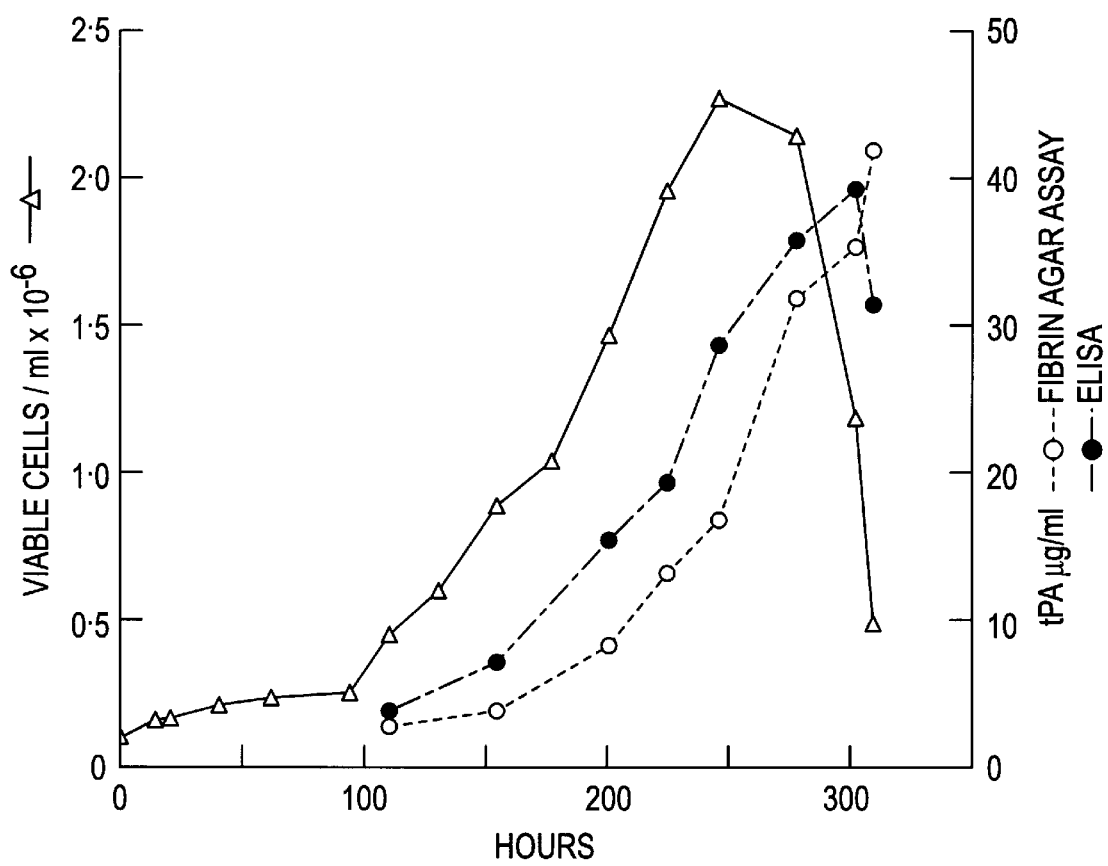
FIG. 3 is a graph showing profiles for growth and tPA synthesis by pRI 1/10 cells in an air lift fermenter (Viable cells ▵; tPA determined by ELISA ●; tPA determined by fibrin agar assay ○).

1. Vector Construction 1.1 Tissue Plasminogen Activator (tPA) cDNA Expression Constructs The methods used in these constructions are as described in detail by Maniatis et al (1982). The tPA specific DNA sequences used in this study were derived from two cDNA clones isolated from a Bowes melanoma library (Harris et al 1986). Plasmid ptPA A3 was constructed by adding HindIII linkers to a 1200 base pair (bp) fragment (nucleotides 9 to 1197, Pennica et al, 1983) of tPA cDNA. The cDNA was then cloned into pAT153 at the unique HindIII site. Plasmid ptPA21 was constructed by cloning a Bgl II cDNA fragment (nucleotides 187 to 2166) into a plasmid with a unique BglII site. A full-length tPA cDNA gene was made by cloning the BglII fragment from ptPA21 into the BglII site of ptPA A3. The resultant plasmid ptPA 3/21 contains 76 bp of 5' non-coding sequence, the complete tPA coding region, 393 bp of 3' non-coding sequence, and a repeat segment of tPA coding region (nucleotides 187 to 1197), all on a single HindIII fragment. A second plasmid p81/11 was also constructed in which this HindIII fragment was inverted relative to pAT153 sequences.

Plasmid p81/11 was digested with BalI and the BalI fragment containing 116 nucleotides of 3' non-coding sequence, the repeated segment of tPA coding region, and some pAT 153 sequences were removed leaving plasmid pBSI. Single BamHI and SalI restriction enzyme sites were re-introduced into pBSI by ligation of the 275 bp BamHI/SalI fragment from pAT 153, whose cohesive termini had been filled in with DNA polymerase; into the BalI site. Depending upon the orientation in which the fragment was inserted, either a SalI site (pBS17) or a BamHI site (pBS18) was reformed at the 3' end of the tPA gene. Plasmid pBS18 was the precursor for all tPA cDNA expression constructs.

1.2 Mouse Metallothionein (MMT-I) Promoter

Clone 28 (Dr. D. Hamer; National Institute of Health, Bethesda, Md, U.S.A.) has the entire SV40 genome cloned into a BamHI site and a 3.8 Kb EcoRI fragment containing the mouse metallothionein I (MMT-I) gene (Hamer and Walling, 1982) cloned into an EcoRI site. This plasmid provided the MMT-I promoter (MMT) in tPA expression constructs. The unique BglI site, 4 bp upstream of the translation start point (Glanville, et al, 1981), was converted to a HindIII site using the oligonucleotide CCAAGCTTGG.

A 2.0 Kbp HindIII fragment derived from clone 28 containing the MMT promoter was cloned into the unique HindIII site of pBS18 resulting in the formation of a transcriptional fusion between the MMT promoter and tPA coding sequences. This plasmid was called pBS18M3. A BamHI/BclI fragment of 243 bp derived from clone 28 and containing the SV40 polyadenylation site was inserted into the BamHI site of pBS18M3. The polyadenylation site was orientated in the early to late direction thus recreating a BamHI site distal to the tPA gene. This plasmid was denoted p3.16.

1.3 Rous Sarcoma Virus and Moloney Murine Leukaemia Virus Long Terminal Repeats

The long terminal repeats (LTR) of the Rous sarcoma virus (RSV) and Moloney murine leukaemia virus (Mo MLV) were isolated as ClaI/HindIII fragments from pRSV-cat (Gorman et al. 1982) and p836 (Hoffmann et al, 1982), respectively. In the former case, a MboII site was converted to a ClaI site using the oligonucleotide GGATCGATCC and in the latter case, a SmaI site was converted to a ClaI site using the oligonucleotide GGATCGATCC and in the latter case, a SmaI site was converted to a HindIII site using the oligonucleotide CCAAGCTTGG. The fragments were individually cloned into p3.16, previously cut with ClaI and HindIII, so that the MMT promoter could be replaced by a retrovirus LTR promoter. The resultant plasmids were called pRSV3 (containing the RSV LTR) and pZAP7 (containing the MoMLV LTR). (see FIG. 1).

1.4 SV40 Late Promoter

The plasmid containing the SV40 late promoter driving tPA was constructed using p3.16 as the basic vector. The SV40 late promoter was isolated from pSV2 neo by PvuII digestion, followed by addition of HindIII linkers, and subsequent HindIII digestion. The SV40 late promoter fragment so generated was purified by gel electrophoresis and used to replace the HindIII promoter fragment of MMT from plasmid p3.16. The plasmid generated was denoted p6. (FIG. 1).

1.5 Comparative Example—Immunoglobulin Promoter/Enhancer

A plasmid containing an immunoglobulin promoter/enhancer combination was constructed using pAT153 as the basic vector (Twigg and Sherratt, 1980). The EcoRI-BamHI region in pAT153 was replaced by the Ig heavy chain enhancer (Ig en) on a XbaI-EcoRI fragmment, (Gillies et al, 1983) converted to an EcoRI fragment by addition of EcoRI linkers. The Ig en was cloned in the sense orientation relative to an Ig heavy chain promoter (Ig Pro) isolated as a 1.3 kb EcoRI-NcoI fragment. This promoter fragment is derived from phage clone VNPB-186, (Bothwell et al, 1981) with its NcoI site filled in by polymerase and converted to a BglII site by linker addition, resulting in generation of vector pMI205. The tPA gene was introduced into this vector as a BamHI fragment. This was isolated from pBS18 as a BamHI-HindIII fragment followed by addition of BamHI linkers. The tPA BamHI fragment was introduced into the BglII site of pMI205 creating pMI205tPA.

The five plasmids p3.16, pRSV3, pZAP7, p6 and pMI205 (FIG. 1) were the direct precursors of the tPA expression constructs, and also the plasmids used in transient assays for tPA production.

1.6 Selection Markers and Other Functional Fragments

The genes responsible for conferring dominant selection were derived from pSV2 neo (Southern and Berg, 1982), pSV2dhfr (Subramani et al, 1981) and psV2gpt (Mulligan and Berg, 1981).

The resistance to antibiotic G418 conferred by the transcription unit in pSV2 neo ('neo'), was used in the majority of the described constructs. In order for the 'neo' transcription unit to be used it was recloned to be contained within both a BamHI and also a HindIII fragment.

The starting point for these vector constructs was pSV2 βglobin (FIG. 1), (Southern and Berg, 1982). The vector's HindIII site was converted into a BglII site followed by removal of the resultant BglII fragment containing βglobin. The resultant plasmid, pSV2 BglII formed the basis of the next step-conversion of the PvuII site into a HindIII site generating plasmid pSV3M.

The introduction of the 'neo' gene into pSV3M was via replacement of the BglII-BamHI poly A-splice gene fragment by a BglII-BamHI fragment isolated from pSV2 neo. The resultant plasmid, pSV3Mne, now contained the SV40 early promoter driving the expression of the 'neo' gene without a poly A sequence, contained within a HindIII-BamHI fragment. The HindII and BamHI sites of pSV3Mne were separately converted into BamHI and HindIII sites respectively resulting in the generation of plasmids pSV3Bne and pSV3MMne (FIG. 1) respectively.

In order to produce a suitable gene fragment for the use of the xanthine-guanine phosphoribosyltransferase (gpt) gene from pSV2gpt (Mulligan and Berg, 1981), conferring dominant selection in the presence of mycophenolic acid and xanthine (Morrison and Oi, 1984), we replaced the BglII-BamHI fragment of pSV3Mne containing the 'neo' gene with the BglII-BamHI fragment of pSV2 gpt containing the gpt gene. The resultant plasmid pSV3 gpt contains the SV40 early promoter driving expression of gpt with a poly A-splice from SV40 at the 3' end on a HindIII-BamHI fragment. This vector's HindIII site was then converted to a BamHI site, producing plasmid pSV3 Bgpt, providing a suitable BamHI fragment for use in the described vectors.

To enable a study of the utility of amplification within myeloma cells, we made use of the mouse dihydrofolate reductase (dhfr) cDNA gene as contained in pSV2 dhfr (Subramani et al, 1981).

In order to produce a gene fragment of the SV40 early promoter and dhfr suitable for our vectors, we converted the PvuII site of pSV2 dhfr to a BamHI site by linker addition, generating plasmid pDB. pDB contains a BamHI fragment containing the SV40 early promoter driving the dhfr gene with the SV40 poly A- splice sequence at the 3' end.

Plasmid BMTHI (Dr. G. N. Pavlakis; National Cancer Institute; Frederick, Md.) contains the entire BPV-1 genome and the complete MMT-I gene on a BamHI/SalI fragment. A second plasmid, pBMT13, was constructed from pBMTHI in which the BamHI site was converted to a SalI site and the SalI site was converted to a BamHI site.

Initial vectors were based on BPV vectors in order to examine the potential value of these. The studies with pBMT13 demonstrated that heavy metal selection with myeloma cells was not useful. This raised the need for another selection system within BPV. In order to construct BPV vectors conferring dominant selection in myeloma cells, we introduced the 'neo' gene cassette from pSV3MMne isolated as a HindIII fragment enabling the direct replacement of the MMT-I gene in pBMT13. This replacement of MMT-I gene resulted in two new BPV-based plasmid vectors, p2012SneR and p2012SneR and p2012SneL, containing the SV40 early promoter driving the 'neo' gene as a HindIII insert, in both orientations relative to BPV. These BPV vectors formed the basis of the vectors tested in myeloma cells using the tPA plasmids described above p6, p316, pRSV3 and pZAP7. The resultant plasmids PAC1, pAC2, pAC5, and pAC6 were generated by replacing the BamHI-SalI pAT153 sequence with BamHI-SalI fragments from p6, p316, pRSV3 and pZAP7.

Further constructs were made without the use of BPV. In these later constructs, use was made of the BamHI fragments from pSV3ne, pSV3 Bgpt and pDB conferring a dominant selectable marker on the plasmids.

In order to use pRSV3 for generation of stable cell lines, in the absence of a BPV vector conferring selection, a selection marker was introduced into the BamHI site. The selection cassette used was the BamHI fragment from pSV3Bne, producing plasmids pPRI and pPRII containing the BamHI fragment in both orientations. In addition to the 'neo' gene, the BamHI selection cassette from pSV3 Bgpt and pDB were also introduced at the BamHI site, resulting in the production of pRSG containing the gpt gene and pRSD3 containing three or more dhfr gene cassettes.

To make use of the SV40 later promoter driving tPA expression, in the absence of BPV, similar constructions as above were made. The BamHI gpt gene cassette from pSV3 Bgpt was introduced producing p6 gpt. The utility of the p6 gpt vector was further enhanced by the introduction into partial BamHI-digested p6 gpt the dhfr BamHI expression cassette, giving rise to p6GD.

2. Transfections

The cell lines used for transfections were SP2-OAg 14 (Shulman et al, 1978); NSO, this is a subline of P3/NS1/1 Ag4.1 (Kohler et al, 1978); that does not express the intracellular light chains (M. Clark, B. W. Weight and C. Milstein); 001; a BALB/cxNSO hybridoma (Sherwood, M. unpublished) and YB2/3.0 Ag20 (U.K. Patent GB2079313). These cell lines were maintained in Dulbecco modified Eagle's medium (DMEM, Gibco Ltd., U.K.) with penicillin (50 U/ml), streptomycin (50 µg/Ml), 1 mM pyruvate, 2 mML- glutamine and heat inactivated foetal calf serum (10%).

In order to introduce DNA into myeloma cells we have made use of the standard methods using DEAE-Dextran, CaPO4 and electroporation (Banerji et al, 1983; Graham and Van der Eb, 1973; Potter et al, 1984). The majority of our transfections were made using a modification to the DEAE-Dextran method making use of dimethyl sulphoxide (DMSO) stock (Lopata et al, 1984) and chloroquinine (Lathman and Magnusson, 1983) to improve transfections.

The cells, after transfections, were typically left for 24 hours before selection was introduced. The transfections with plasmid constructs containing the 'neo' gene cassette from either pSV3Bne or pSV3MMne were selected using the antibiotic G418 (Geneticin Gibco Ltd., U.K. [Schering Corp. U.S. Pat. Nos. 3,959,254, 3,997,403]) at a concentration of 1.4 mg/ml.

The plasmids containing the gpt gene cassette from pSV3 Bgpt were selected for by supplementing the culture medium with 200 µg/ml xanthine, 5 µg/ml mycophenolic acid (Gibco, U.K.) and 13.6 µg/ml of hypoxanthine.

The selection of plasmids containing the dhfr gene cassette from pDB was carried out at 150 nM methotrexate (Page, 1985).

In the case of transfection with p6GD, cell lines were initially selected making use of the gpt gene cassette followed by the utilisation of the dhfr gene cassette for amplification.

The cells, after the introduction of the selection, were allowed to incubate again for a further 24–48 hours before being plated out into microtitre dishes for clone selection. These microtitre dishes were typically incubated for 2–3 weeks before the first clones appeared. The clones were allowed to grow up to saturation (turning the culture media phenol red to yellow) prior to assaying the supernatants or to expansion into 24 well tissue culture dishes. The cell lines from those transfections which demonstrated useful levels of tPA production (greater than 100µ/ml) were stored as frozen stocks in liquid nitrogen after supplementing the culture medium with 10% DMSO. These cell lines were also recloned and selected high producers also stored as above.

Quantitation of tPA Protein

The tPA from cell lines was either assayed via fibrinolysis or by an enzyme linked immunosorbent assay (ELISA).

Active tPA protein in the medium was assayed using a fibrin-agarose plate assay as modified by Cederholm-Williams. LGT agarose, 20 mg/ml, in 0.1 M Tris (pH 7.4), 0.15 M NaCl, and 2 mM $CaCl_2$ was melted and cooled to 55° C. An equal volume of fibrinogen, 2 mg/ml in 0.9% (w/v) NaCl, and human plasminogen to a final concentration of 10 µg/ml were added. Fibrin polymerisation was initiated by adding bovine thrombin to 0.12 units/ml. The mixture was poured on polyester sheets and allowed to set. Dilutions of samples and dilutions of a urokinase standard solution of known concentration (5 µl volume) were added to wells punched in the gel and the plates were incubated at 37° C. for 17 to 20 hours in a humidified chamber. The diameters of the areas of lysis were measured. A standard curve was drawn from the urokinase data by plotting the log of the diameter squared against the log of the concentration. The amount of activity in the samples was determined from the standard curve. Within the 10 to 100 units/ml range, urokinase was shown to be a suitable standard for estimating tPA activity.

Total tPA protein in culture medium from the transfected cell line was assayed using an ELISA. The ELISA was performed in Nunc Immuno assay plates (Nunc, Denmark) coated for 1 hour at 37° C. with 2 µg/ml of a goat polyclonal anti tPA (Biopool, Sweden) in 0.05M sodium carbonate (pH 9.6). These plates were blocked for 1 hour at 37° C. with 0.5% casein Hammerstem in 0.05M sodium carbonate (pH 9.6). These coated and blocked microtitre plates, and plates at other wash stages were washed with phosphate buffered saline, with 0.02% Tween 20. Samples for assay were diluted into sample buffer (0.1M Tris-HCl Ph 7.0, 150 mM NaCl, 0.5% casein and 0.02% Tween 20). The standard used in this assay was two chain tPA (Biopool, Sweden). Samples were introduced at 100 µl per well and incubated for 1 hour at room temperature with shaking. The plates were then washed and 1 µg/ml of MAC010, a mouse monoclonal antibody to tPA, in sample buffer added to each well (100 µl). These were incubated for 1 hour at room temperature with shaking. The plates, after incubation with the monoclonal antibody, were washed and 100 µl of goat anti-mouse IgG Fc specific peroxidase conjugate was added to each well and incubated for 1 hour at room temperature with shaking. The plates, after incubation with conjugate, were washed and then developed as described (Bos et al, 1981).

Transient Assays of tPA Production in Myeloma Cells

In order to evaluate the ability of our plasmid constructs to direct the expression of eukaryotic gene products, we adapted the fibrin overlay assay for plasminogen activators into a rapidly sensitive and consequently powerful transient assay system (Jones et al, 1975; Kenten et al, 1986).

The plasmids used for these transient assays of tPA production were those described earlier namely:

p3.16 containing the mouse metallothionein promoter, pRSV3 containing the RSV LTR, pZAP7 containing the MoMLV LTR, p6 containing the SV40 late promoter and pMI205 tPA containing an immunoglobulin promoter/enhancer combination.

The transfections were carried out using the DEAE-Dextran method as described and the cells were put directly into the tPA assay described below.

For the tPA assay, transfected cells were scraped off the plate (about $5 \times 10^6$) and 10% of the cells taken and washed twice in serum-free DMEM (Gibco), 1 mM pyruvate, 50 IU/ml penicillin, 50 µg/ml streptomycin (P/S), 2 mM L-glutamine (Gln). These cells were then suspended in 7 ml of 70% DMEM as above, supplemented with 10% (v/v) acid treated foetal calf serum (FCS); 30% (v/v) Hanks balanced salts (Gibco), supplemented with 2.5% low gelling temperature agarose (Sigma Ltd.) at 42° C. This suspension was then supplemented with 0.5 units of thrombin (from bovine plasma 500 U/ml, Sigma Ltd.). Finally, 1.5 mls of DMEM, 1 mM pyruvate, P/S, Gln, 10% (v/v) acid treated FCS, 30 mg/ml fibrinogen (from bovine blood, type I-S, Sigma Ltd.) was added and the mixture poured immediately into a 90 mm dish.

These dishes were incubated for times up to 48 hours in order to determine the level of tPA being produced from these transfections. The results were recorded as relative levels of fibrinolytic activity, FIG. 2 shows a typical result.

The results from these transfections demonstrated that for YB2/3.0 Ag20 promoters were ranked: RSV LTR, SV40 late, MoMLV LTR and MMT in descending order of activity. Cell lines SP2/0-Ag14 and a BALB/c×NSO mouse hybridoma demonstrated a ranking of the promoters: SV40 late, RSV LTR, MoMLV LTR and MMT in descending order of activity.

We also tested one immunogloublin promoter in combination with a partially characterised enhancer fragment as described in the vector constructs section above. This gave levels of tPA expression very similar to the MMT promoter in myeloma cell lines.

The results from these assays provide a useful framework on which to base an initial study of cell lines with integrated genes for expression. The transient assay only provides a measure of the promoter strength isolated from the normal gene environment (within the chromosome). Thus one may find differences between results from transient and stable cell-lines in terms of promoter preference.

tPA Producing Cell Lines

The tPA producing cell lines have been derived from the mouse hybridomas SP2/O-Ag14, NSO and the rat hybridoma YB2/3.0-Ag20. These cell lines illustrate the ability of viral promoters to drive the expression of eukaryotic genes in hybridoma and myeloma cell lines.

The mouse hybridoma cell line SP2/O-Ag14 was chosen as it represents a good candidate for a production cell line as it grows well in serum free medium as a suspension. The transfection of this cell line with plasmids aPC1, pAC2, pAC6 and pPRI demonstrated the ability to obtain cell lines expressing tPA from SP2/O-Ag14. The results with pAC1, pAC2, pAC6 and pPRI demonstrate the potential of the MMT, RSV LTR and Mo MLV LTR promoters to drive expression of eukaryotic proteins in this cell line.

The results for SP2/O-Ag14 (Maximum Levels) were as follows:

| Plasmid | Promoter | Maximum U/ml of Culture |
| --- | --- | --- |
| pAC2 | MMT | 4 U/ml |
| pAC1 | Mo MLV LTR | 50 U/ml |
| pAC6 | RSV LTR | approx. 10 U/ml |
| pPRI | RSV LTR | 4 U/ml |

The other mouse hybridoma cell line, NSO, also has the desirable growth characters of SP2/O-Ag14. One plasmid vector (p6GD) was transfected into NSO to generate cell lines. These cell lines were demonstrated to synthesise tPA up to 27 U/ml under the influence of the SV40 late promoter.

The rat hybridoma studies was the YB2/3.0-Ag20 cell line which has proved valuable in generating high producing hybridoma cell lines. This cell line was productively transfected with pAC1, pAC6, pPRI, p6GD, pRSD3 and p6 gpt demonstrating the ability of the Mo MLV LTR, RSV LTR and the SV40 late promoters to drive expression in this cell line.

The results for the cell lines obtained by transfection are shown below:

| YB2/3.0-Ag20 (Maximum Levels) | | |
| --- | --- | --- |
| Plasmid | Promoter | Maximum Units/ml of Culture |
| pAC1 | Mo MLV LTR | 50 |
| pAC6 | RSV LTR | 200 |
| pPRI | RSV LTR | 900 |

| YB2/3.0-Ag20 (Maximum Levels) | | |
| --- | --- | --- |
| Plasmid | Promoter | Maximum Units/ml of Culture |
| P6GD | SV40 late | +Ve |
| p6 gpt | SV40 late | 6.6 |
| pRSD3 | RSV LTR | 45 |

Amplification

The amplification of the gene copy number is a recognised route to improve the production of protein from expression systems. This has been largely due to the recognition of gene amplification as a mechanism naturally found in various specialised tissues or species (Schimke, 1984). This mechanism has been utilised in eukaryotic expression systems but only significantly in Chinese hamster cell lines (Kaufman et al, 1983). The best characterised aplification system is that based on dhfr and ethotrexate (Schimke, 1984). Thus with this background it was of interest to see if co-amplification of gene expression could be made to function usefully in the mouse and rat hybridoma/myeloma cell lines.

The study carried out made use of the plasmid construct pRSD3 and the cell line YB2/3.0-Ag20. This plasmid vector was transfected into YB2/3.0-Ag20 and clones selected using 150 nM methothrexate. These cell lines were screened and producing clones were selected to grow on higher and higher levels of methotrexate using recognised methods (Kaufman, et al, 1983). The cell lines were stored at the start of the amplification and at intervals during the amplification. The range of expression for tPA was typical with a wide spectrum of activity being observed in the initial cell lines isolated.

Our results demonstrated that as resistance to methotrexate increased so did the level of tPA production demonstrating that indeed co-amplification with hybridoma/myeloma cell lines was valuable.

This utility is best illustrated with our best example cell line YO/pRSD3/2D. This started at 45 U/ml tPA growing in 150 nM methotrexate. The level of tPA production was raised to 5800 U/ml growing in 3 $\mu$M methotrexate after 5 months.

In order to prove the value of these transfected cells in large scale culture, one cell line was selected for evaluation in a small airlift fermenter. The cell line chosen was YB2/3.0Ag20 transfected with pPRI, a clone which had demonstrated high levels of production in stationary culture, pRI 1/10.

Fed Batch Culture of Cell Line pPRI 1/10 in an Airlift Fermenter

The aim of this experiment was to access growth and tPA synthesis by cell line pPRI 1/10 in a production type cell culture reactor.

The cell reactor used was an aiflift fermenter (ALF) of 5 litres working volume with automatic control of dissolved oxygen tension (DOT), pH and temperature. DOT was controlled by regulated injection of air or oxygen into a sparged ballast gas of nitrogen or air. pH was controlled by regulated injection of carbon dioxide into this gas mixture or by applying a pumped feed of alkali to the culture. Temperature was controlled by a flow of temperature regulated water to the reactor jacket.

Cell stocks of the cell line pPRI 1/10 were routinely grown in roller bottle culture in a growth medium consisting of Dulbecco's modification of Eagle's medium (DMEM) supplemented with heat-inactivated foetal calf serum (FCS) at 10% vol/vol.

Medium for the ALF culture was a serum-free formulation consisting of a DMEM base supplemented with albumin, insulin, transferrin, ethanolamine, choline, vitamins, trace metals and a shear protective polymer.

Cell inoculum for the ALF culture was grown in serum-supplemented medium. The cells were sedimented by centrifugation and resuspended in the serum-free growth medium prior to inoculation into the ALF. During the ALF culture supplementing nutrients were added. These consisted of:

a) a shot addition of glutamine to give an increase of 2 mM final concentration in the culture b) a shot addition of the "insoluble" amino acids tryptophan, tyrosine and cysteine c) a pumped feed consisting of glucose choline and the "soluble" amino acids.

Samples were removed from the culture at daily intervals. Cell counts were performed using a modified Fuchs Rosenthal counting chamber and cell viability was assessed by exclusion of Trypan Blue stain. Aliquots of culture supernatant were snap frozen in liquid nitrogen and then stored at −70° C. for subsequent quantitation of tPA by tPA ELISA and by fibrin agar plate assay.

FIG. 3 shows profiles for growth and tPA synthesis by pPRI 1/10 cells in airlift culture. Cells attained a maximum viable population density of $2.2 \times 10^6$/ml and a maximum total population density of $4 \times 10^6$ml. tPA was synthesised throughout the duration of the culture, reaching a maximum concentration of 42 ug/ml measured by fibrin agar plate assay and 38 ug/ml measured by tPA ELISA. The close agreement between ELISA (which would detect both active and inactive tPA) and the fibrin agar plate assay indicates that the tPA synthesized was fully active.

The invention is described by way of example only, and modifications of detail may be made within the scope of the invention.

REFERENCES

Southern, P. J. and Berg, P., Transformation of mammalian cells to antibiotic resistance with a bacterial gene under control of the SV40 Early Region Promoter, J. Mol. Applied Genetics, 1982; 1:327–341.

Subramani, S., Mulligan, R. and Berg, P. Expression of the mouse dihydrofolate reductase complementary deoxyribonucleic acid in Simian virus 40 vectors. Mol. Cell. Biol. 1981; 1: 854–864.

Mulligan, R. C., and Berg, P. Selection for animal cells that express the Escherichia Coli gene coding for xanthine-guanine phophoriboxyltransferase. Proc. Nat. Acad. Sci. USA, 1981, 78: 2072–2076.

Banerji, J., Olson, L. and Schaffner, W. A. Lymphocyte specific cellular enhancer is located downstream of the joining region in immunoglobulin heavy chain genes. Cell (1983) 33: 729–740.

Graham, F. L., and A. J. van der Eb. A new technique for the assay of infectivity of human adenovirus 5 DNA. Virology (1983) 52: 456–467.

Potter, H., Weir. L., and Leder, P. Enhancer-dependent expression of human R immunoglobulin genes introduced into mouse pre-$B_2$ lymphocytes by electroporation. Proc. Natl. Acad. Sci USA (1984) 81: 7161–7165.

Lopata, M. A., Cleveland, D. W., and Sollner-Webb, B. High level transient expression of a chloramphenicol acetyl transferase gene by DEME-dextran mediated DNA transfection coupled with a dimethyl sulfoxide or glycerol shock treatment. Nucleic Acids Res. (1984) 12: 5707–5717.

Luthman, H. and Magnusson, G. High efficiency polyoma DNA transfection of chloroquinine treated cells Nucleic Acids Res. (1983) 11: 1295–1308.

Page, M. J., Expression of amplified human beta interferon genes using heavy metal induction in Chinese hamster ovary cells. Gene (1985) 37: 139–144.

Jones, P., Benedict, W., Strickland, S. and Reich, E. (1975). Fibrin overlay methods for the detection of single transformed cells and colonies of transformed cells. Cell 5: 323–329.

Kenten, J. H., Wood, C. R., Stephens, P. E., Bendig, M. M., Boss, M. A. and Hentschel, C. C. A sensitive non-destructive assay for transfected genes. DNA (1986) June, (in Press).

Bos, E. S., Vander Doden, A. A., Van Roog, N. and Schmurs, A. H. W. M. (1981) J. Immunoassay 2, 187–204.

Twigg, A. and Sherratt, D. (1980) Trans-complementable copy-number mutants of plasmid ColE1. Nature 283: 216–218.

Maniatis, T., Fritsch, E. F. and Sambrook, J. (1982) Molecular cloning (a laboratory manual), Cold Spring Harbor Laboratory.

Pennica, D., Holmes, W. E., Kohr, W. J. Harkins, R. N., Vehar, G. A. Ward, C. A., Bennett, W. F., Yelverton, E., Seeburg, P. H., Heyneker, H. L., Goeddel, D. V. and Collen D. (1983). Cloning and expression of human tissue-type plasminogen activator cDNA in E. coli. Nature 301: 214–221.

Bothwell, A. L. M., Paskind, M., Reth, M., Imanishi-Kari, T., Rajewsky, K. and Baltimore, D. (1981). Heavy chain variable region contribution to $NP^b$ family of antibodies: Somotic mutation evident in 2b. Cell 24: 625–637.

Gillies, S. D., Morrison, S. L., Oi, V. T. and Tonegawa, S. (1983). A tissue-specific transcription enhancer element is located in the major intron of rearranged immunoglobulin heavy chain gene. Cell 33: 717–728.

Lusky, M., and M. Botchan. 1981. Inhibition of SV40 replication in simian cells by specific pBR322 DNA sequences. Nature 293: 79–81.

Hoffmann, J. W., Steffen, D., Gusella, J., Tabin, C. Bird, S., Cowing, D., and Weinberg R. A., 1982. DNA methylation affecting the expression of murine leukemia proviruses. J. Virol 44: 144–157.

Hamer, D., and Walling, M (1982). Regulation in vivo of a cloned mammalian gene: cadmium induces the transcription of a mouse metallothionein gene in SV40 vectors. J. Mol. Appl. Genet. 1: 273–288.

Harris, T. J., Patel, J., Stephens. P., Kenten, J. Marston, F. A., Little, s., Emtage, J. S., Opdenakker, G., Volckaert, G., Rombauts, U., Billau, A., and De Somer, P. 1986. Cloning of cDNA coding for human tissue plasminogen activator and its expression in recombinant prokaryotic and eukaryotic cells.

Glanville, N., Durnam D. M., and Palmiter R. D., 1981. Structure of mouse metallothionein-I gene and its mRNA Nature 292: 267–269.

Gorman, C. M., Merlino, G. T., Willingham M. C., Pastan, I. and Howard, B. M., 1982. The Rous Sarcoma virus long terminal repeat is a strong promoter when introduced into a variety of eukaryotic cells by DNA-mediated transfection. Proc. Natl. Acad. Sci. USA 79: 6777–6781. Kohler, G., Howe, S. C., and Milstein, C. (1976). Eur. J. Immunol. 6: 292.

Schimke, R. T. Gene amplification in cultured animal cells (1984) Cell 37: 705–713.

Kaufman, R. J., Wasley, L. C., Spiliotes, A. J., Gossels, S. D., Latt, S. A., Larsen, G. A. and Kay, R. M. (1983) Mol. Cell. Biol. 5: 1750–1759.

Morrison, S. L., and Oi, V. T., Transfer and expression of immunoglobulin genes (1984) Ann. Rev. Immunol. 2: 239–256.

The cell-lines indicated at page 5 of the specification of this application are on deposit at the American Type Culture Collection, 12301 Parklawn drive, Rockville, Md. 20852, United States of America.

The deposition details are as follows:

| Accession Number | Date of Deposition |
| --- | --- |
| ATCC CRL 1581 | Oct. 22, 1980 |
| ATCC CRL 1662 | Mar. 19, 1982 |
| TIB 18 | Nov. 10, 1981 |

The cell-lines were not deposited by the applicants and no representation is hereby made that the cell-lines are available as of right to the public by virtue of the depositions.

We claim:

1. A process for producing a eukaryotic polypeptide at a level greater than 1 milligram/liter, wherein the method comprises:

transforming a cell line with a vector comprising a viral promoter operably linked to a gene coding for the eukaryotic polypeptide, wherein the cell line is selected from the group consisting of YB2/3.0-Ag20, SP2/O-AG14 and NSO and the viral promoter is selected from the group consisting of a Rous sarcoma virus long terminal repeat, a Moloney murine leukaemia virus long terminal repeat and a Simian virus 40 late promoter; and culturing the transformed cells under conditions such that expression of the gene and production of the eukaryotic polypeptide occurs in the cells.

2. A process according to claim 1, wherein the viral promoter is the Rous sarcoma virus long terminal repeat.

3. A process according to claim 2, wherein the cell line is YB2/3.0-Ag20.

4. A process according to claim 2, wherein the cell line is SP2/O-Ag14.

5. A process according to claim 1, wherein the viral promoter is the Moloney virus murine leukaemia virus long terminal repeat.

6. A process of claim 5, wherein the cell line is YB2/3.0-Ag20.

7. A process according to claim 5, wherein the cell line is SP2/O-Ag14.

8. A process according to claim 1, wherein the viral promoter is the Simian virus 40 late promoter.

9. A process of claim 8, wherein the cell line is YB2/3.0-Ag20.

10. The process according to claim 8, wherein the cell line is SP2/O-Ag14.

* * * * *